United States Patent
Focke et al.

(10) Patent No.: US 6,226,078 B1
(45) Date of Patent: May 1, 2001

(54) DEVICE FOR CHECKING UNITS COMPOSED OF A PLURALITY OF INDIVIDUAL OBJECTS, MATERIAL LAYERS OR THE LIKE

(75) Inventors: Heinz Focke, Verden; Ralf Sinnerbrink, Kirchlinteln, both of (DE)

(73) Assignee: Focke & Co. (GmbH & Co.), Verden (DE)

( * ) Notice: Subject to any disclaimer, the term of this patent is extended or adjusted under 35 U.S.C. 154(b) by 0 days.

(21) Appl. No.: 09/294,203

(22) Filed: Apr. 20, 1999

(30) Foreign Application Priority Data

Apr. 21, 1998 (DE) .............................................. 198 17 824

(51) Int. Cl.⁷ .......................... G01N 21/00; G01N 21/55
(52) U.S. Cl. ........................................ 356/237.1; 356/445
(58) Field of Search ...................... 356/429, 430, 356/431, 445, 446, 448, 394, 237.1, 238.2, 238.1, 237.2; 250/223 R, 559.37, 559.09, 559.08, 559.19, 559.22; 382/108, 141, 143

(56) References Cited

U.S. PATENT DOCUMENTS

| | | | |
|---|---|---|---|
| 3,473,037 | * 10/1969 | Schmermund | 250/223 |
| 4,053,056 | 10/1977 | Day | 209/73 |
| 4,445,520 | * 5/1984 | Knight et al. | 131/282 |
| 4,486,098 | * 12/1984 | Buchegger et al. | 356/445 |
| 4,644,150 | * 2/1987 | Kuga et al. | 250/223 R |
| 4,682,038 | 7/1987 | Focke | 250/548 |
| 4,767,924 | 8/1988 | Giebel et al. | 250/223 R |
| 5,223,915 | * 6/1993 | Neri | 356/394 |
| 5,235,649 | * 8/1993 | Reda | 382/1 |
| 5,315,366 | * 5/1994 | Inada et al. | 356/238 |
| 5,341,824 | 8/1994 | Fletcher et al. | 131/281 |
| 5,646,733 | * 7/1997 | Bieman | 356/376 |
| 5,686,729 | 11/1997 | Bittar et al. | 250/559.04 |
| 5,966,218 | * 10/1999 | Bokelman et al. | 356/429 |
| 5,969,823 | * 10/1999 | Wurz et al. | 356/386 |

FOREIGN PATENT DOCUMENTS

| | | |
|---|---|---|
| 1 532 268 | 11/1971 | (DE) . |
| 29 19 579 | 12/1979 | (DE) . |
| 36 13 515 | 10/1987 | (DE) . |
| 34 07 168 | 7/1992 | (DE) . |
| 41 00 792 | 7/1992 | (DE) . |
| 44 24 045 | 1/1996 | (DE) . |
| 196 14 920 | 8/1997 | (DE) . |
| 196 42 793 | 4/1998 | (DE) . |
| 197 04 718 | 8/1998 | (DE) . |
| 157 087 | 10/1985 | (EP) . |
| 173 613 | 3/1986 | (EP) . |
| 424 330 | 4/1991 | (EP) . |
| 518 141 | 12/1992 | (EP) . |
| 729 025 | 8/1996 | (EP) . |
| 2709472 | 3/1995 | (FR) . |

* cited by examiner

Primary Examiner—Frank G. Font
Assistant Examiner—Michael P. Stafira
(74) Attorney, Agent, or Firm—Sughrue, Mion, Zinn, Macpeak & Seas, PLLC

(57) ABSTRACT

Device for checking objects composed of a plurality of parts, layers or the like with the aid of a checking set (23) past which the object, in particular a cigarette group (12), a material web or the like is moved, reflected light from the object being picked up by an optoelectronic checking member, specifically by a CCD linear array chip (10) which is arranged transverse to the direction of movement and/or transverse to the longitudinal extent of the object. A profile of the object is taken by the CCD linear array chip (10) by means of regions of different light intensity, and processed in an evaluation unit.

8 Claims, 11 Drawing Sheets

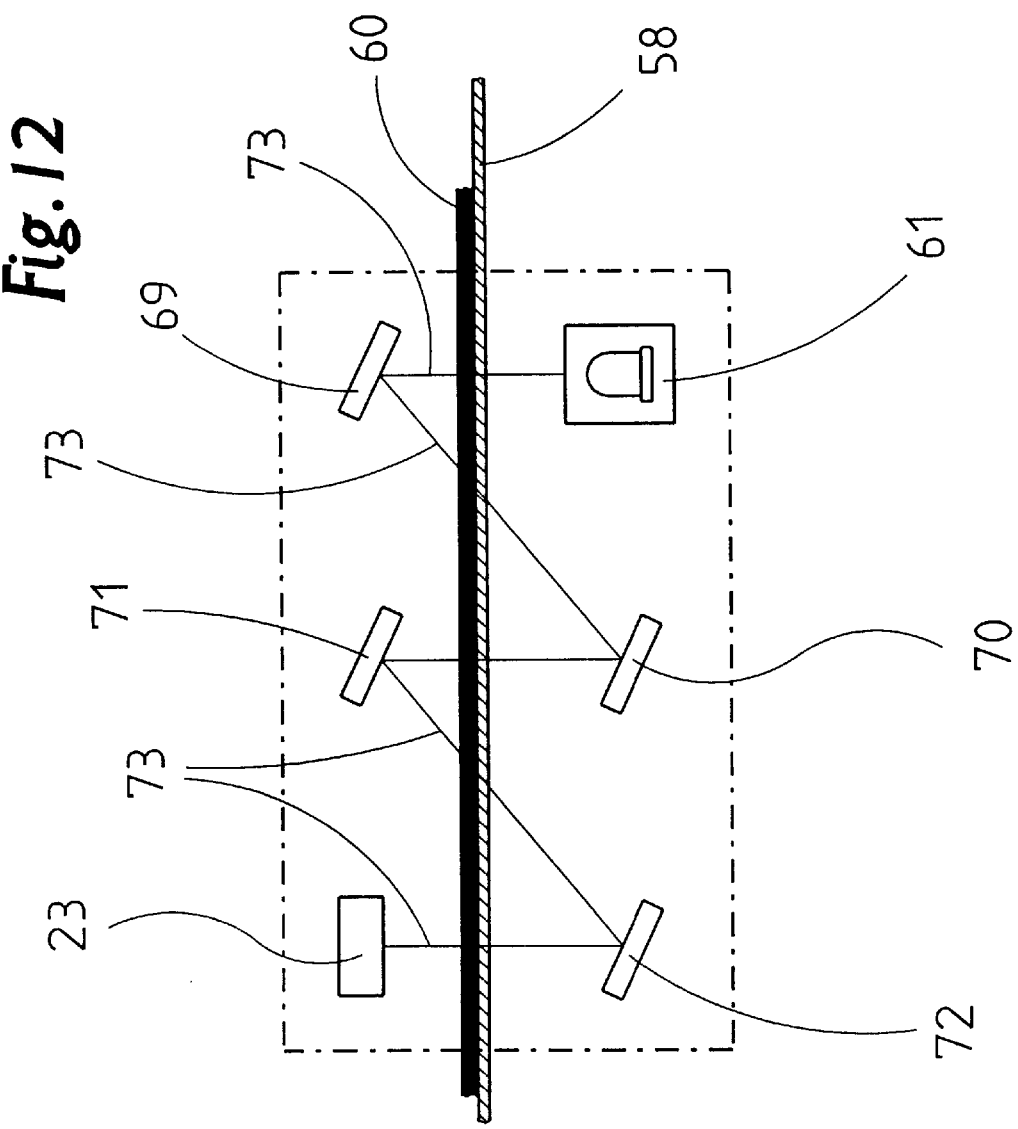
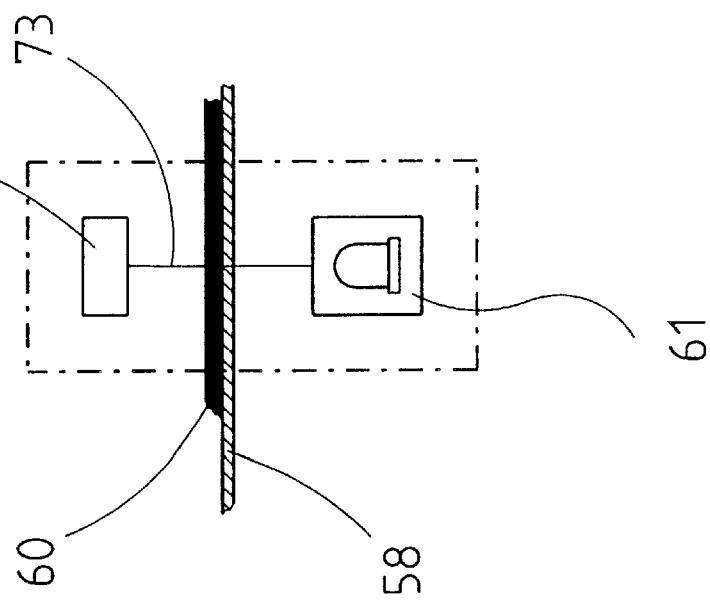

DEVICE FOR CHECKING UNITS COMPOSED OF A PLURALITY OF INDIVIDUAL OBJECTS, MATERIAL LAYERS OR THE LIKE

BACKGROUND OF THE INVENTION

The invention relates to a device for checking units composed of a plurality of parts, in particular of a plurality of individual objects, material layers or the like, for example cigarette groups, bobbins, material webs etc., with respect to complete and/or correct formation in a checking device with a checking member which has a number of light-sensitive checking elements, and with an evaluation device.

In packaging technology, it is necessary, principally in conjunction with packaging machines, for different objects to be checked with respect to correct formation, but also with respect to consumption (for example packaging material). Mechanical checking members previously used are no longer suitable for high-capacity packaging machines of newer generations. For this reason, increasing use is being made of optoelectronic monitoring members in order to check objects with respect to their correct formation continuously or from time to time.

Multiphase monitoring and checking tasks also have to be carried out in packaging cigarettes. Thus, for each cigarette pack it is necessary for the complete and correct assembly of cigarette groups to be monitored, and for the correct configuration of the packaging material to be monitored etc.

SUMMARY OF THE INVENTION

It is the object of the invention to propose a monitoring device which can be used multifariously and delivers correct checking results, even in particular, in the case of packaging machines with quick cycle times.

In order to achieve this object, the device according to the invention is characterized in that its checking member is an CCD linear array chip with a plurality of light-sensitive components as checking elements, and in that the CCD linear array chip is directed transverse to the objects or layers of material webs which are to be checked in such a way that a profile of the object to be checked can be detected by the CCD linear array chip.

A CCD linear array chip is known to be an elongated optoelectronic member with a multiplicity of light-sensitive elements which are arranged next to one another and transmit an electronic signal to an evaluation unit in accordance with the light picked up. According to the invention, such a CCD linear array chip is directed as part of the checking device or the checking member with the longitudinal extent transverse to the object (for example cigarettes), material layers (for example of a bobbin) or material web (a plurality of layers arranged one above another) to be checked. Assigned to the checking device or the checking member are preferably light sources which illuminate the objects to be checked in an optimum fashion. Furthermore, arranged upstream of the CCD linear array chip is preferably an optical system or a lens-diaphragm system, either of which feeds the light picked up to the CCD linear array chip in the dedicated fashion. In the process one or more diaphragms might protect the CCO linear array chip from external light sources and also improve focusing.

The profile taken by the CCD linear array chip is processed in an evaluation device, specifically adjusted by means of a reference image.

BRIEF DESCRIPTION OF THE DRAWINGS

Further details and special features of the invention, in particular preferred exemplary embodiments are explained in more detail below with the aid of the drawings, in which FIG. 11 shows the diagrammatic representation of a checking device for a continuous material web in cross section, and FIG. 12 shows the device in accordance with FIG. 11 in longitudinal section of the material web.

DETAILED DESCRIPTION OF THE INVENTION

Figure 1:
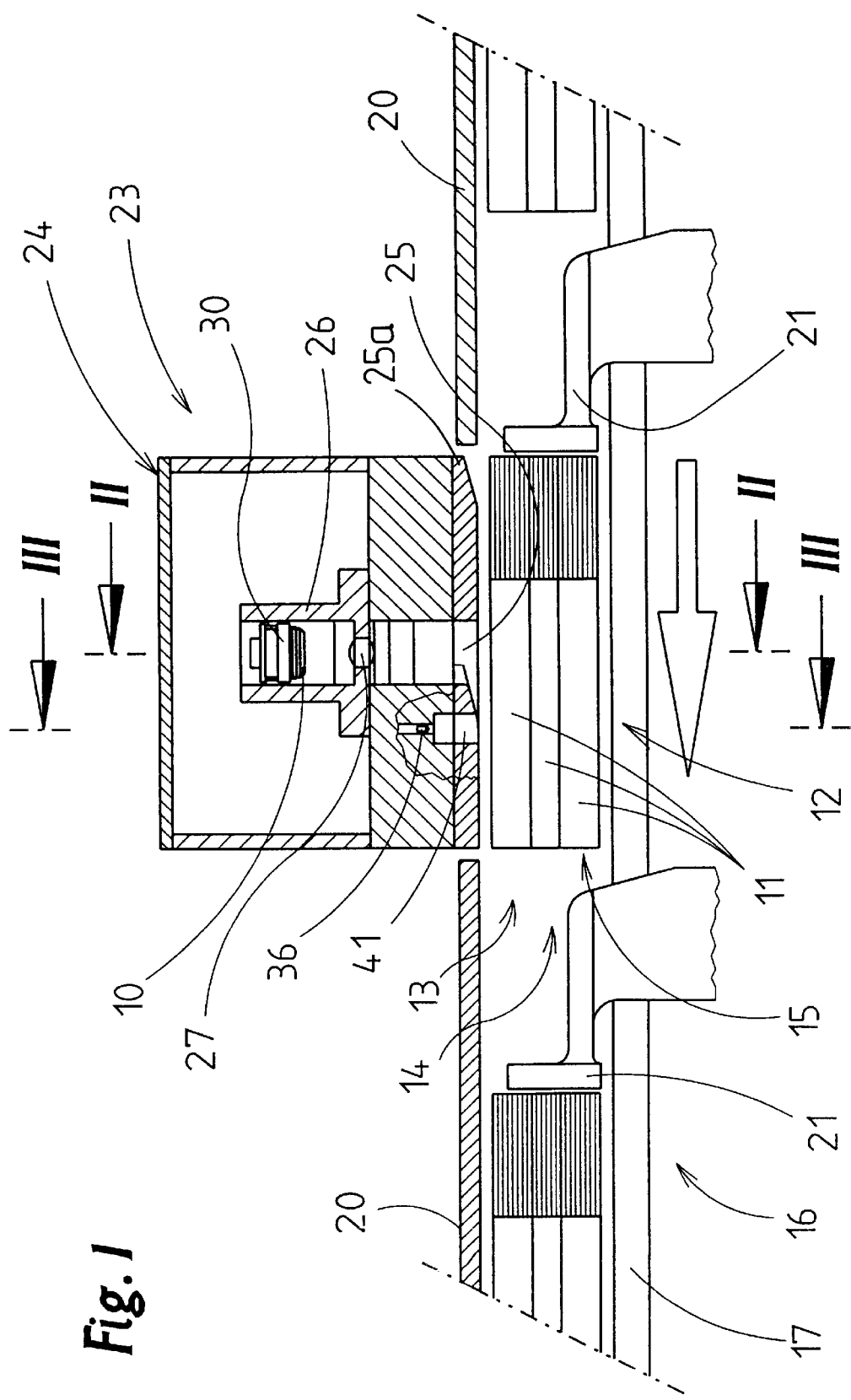
FIG. 1 shows a conveyor for cigarette groups in side view and in longitudinal section with a checking member for the cigarette groups.
Figure 2:
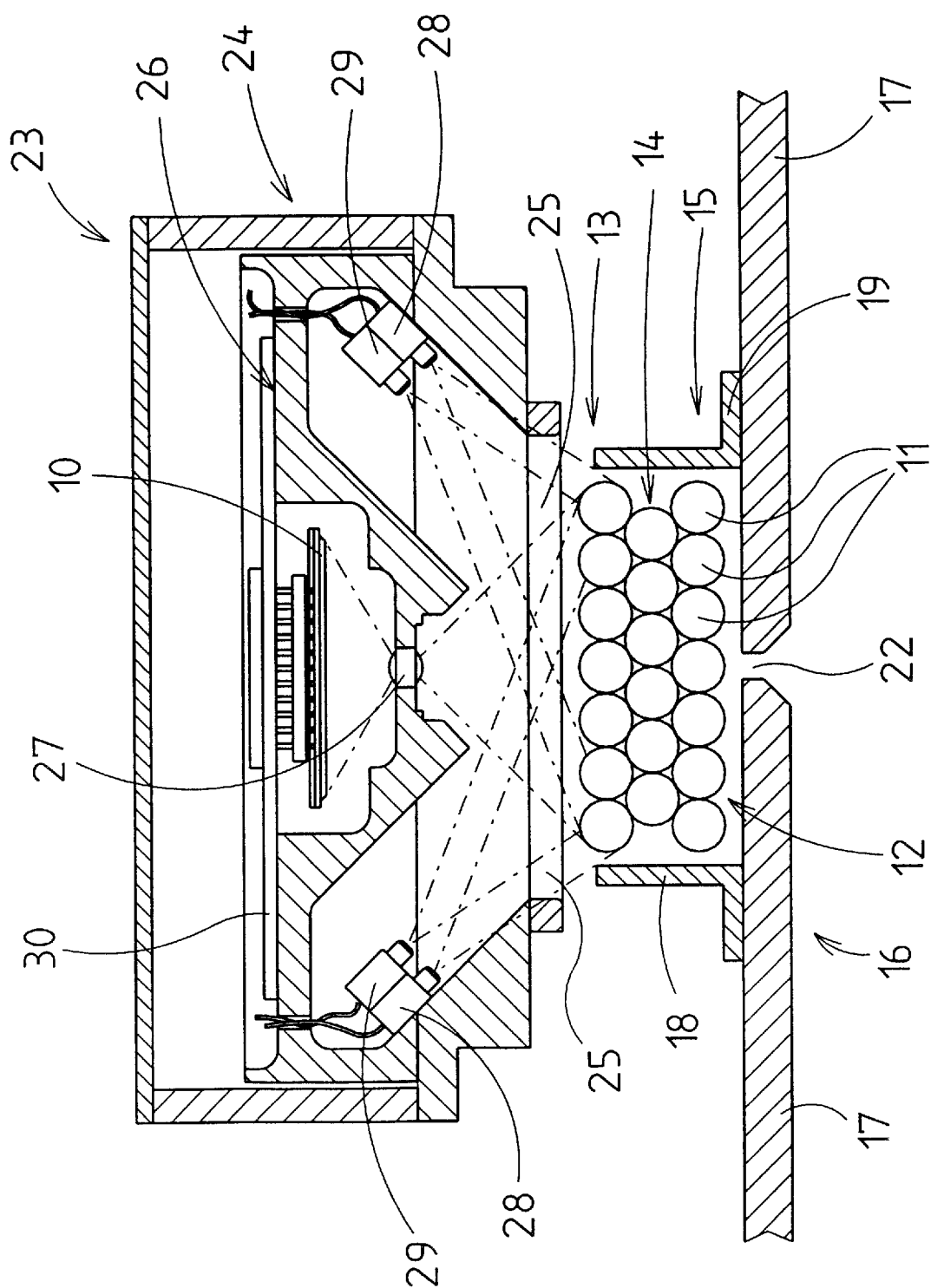
FIG. 2 shows the device in accordance with FIG. 1 in cross section in the planar section II—II of FIG. 1.
Figure 3:
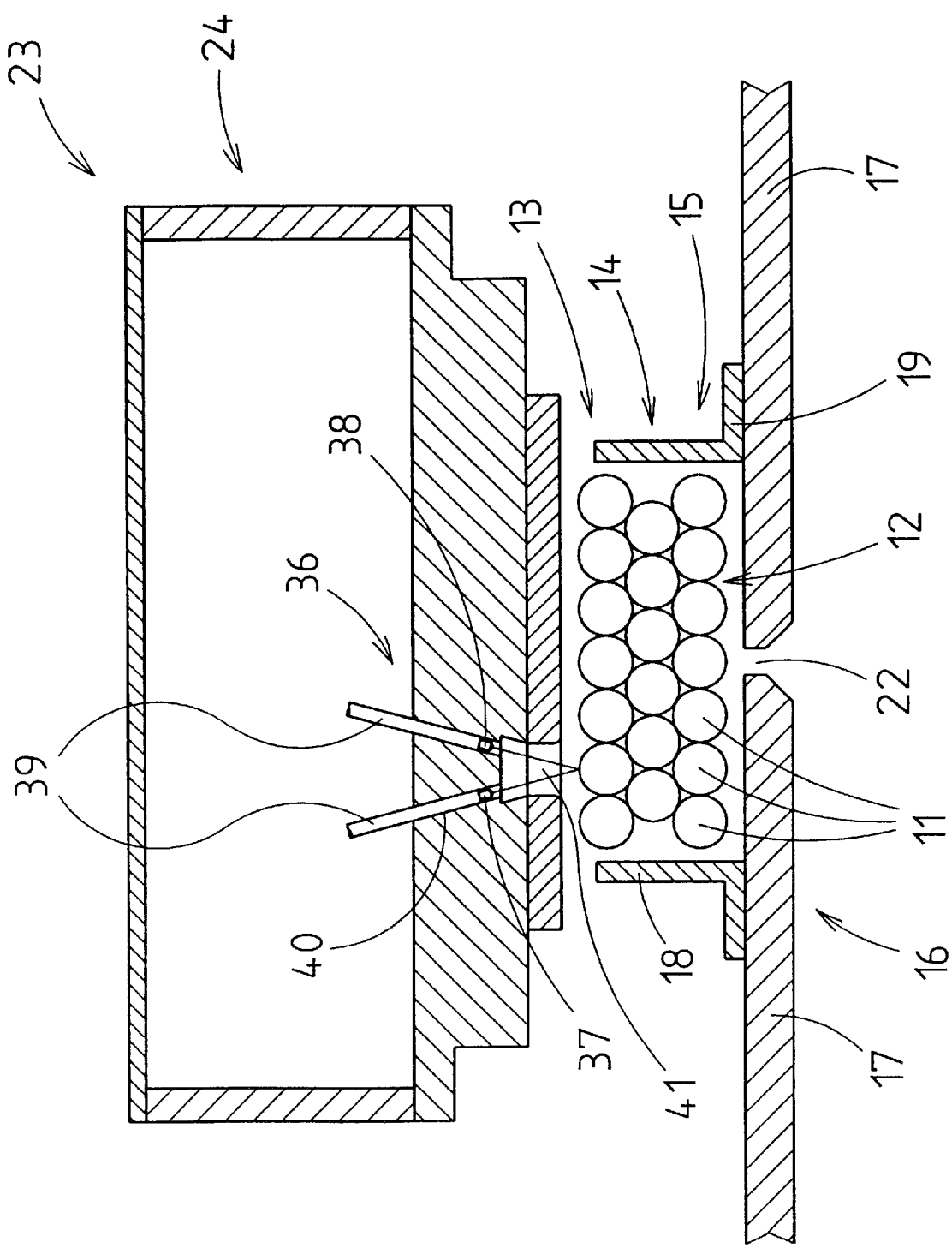
FIG. 3 shows an offset cross section of the device in accordance with FIG. 1 in the planar section III—III.
Figure 4:
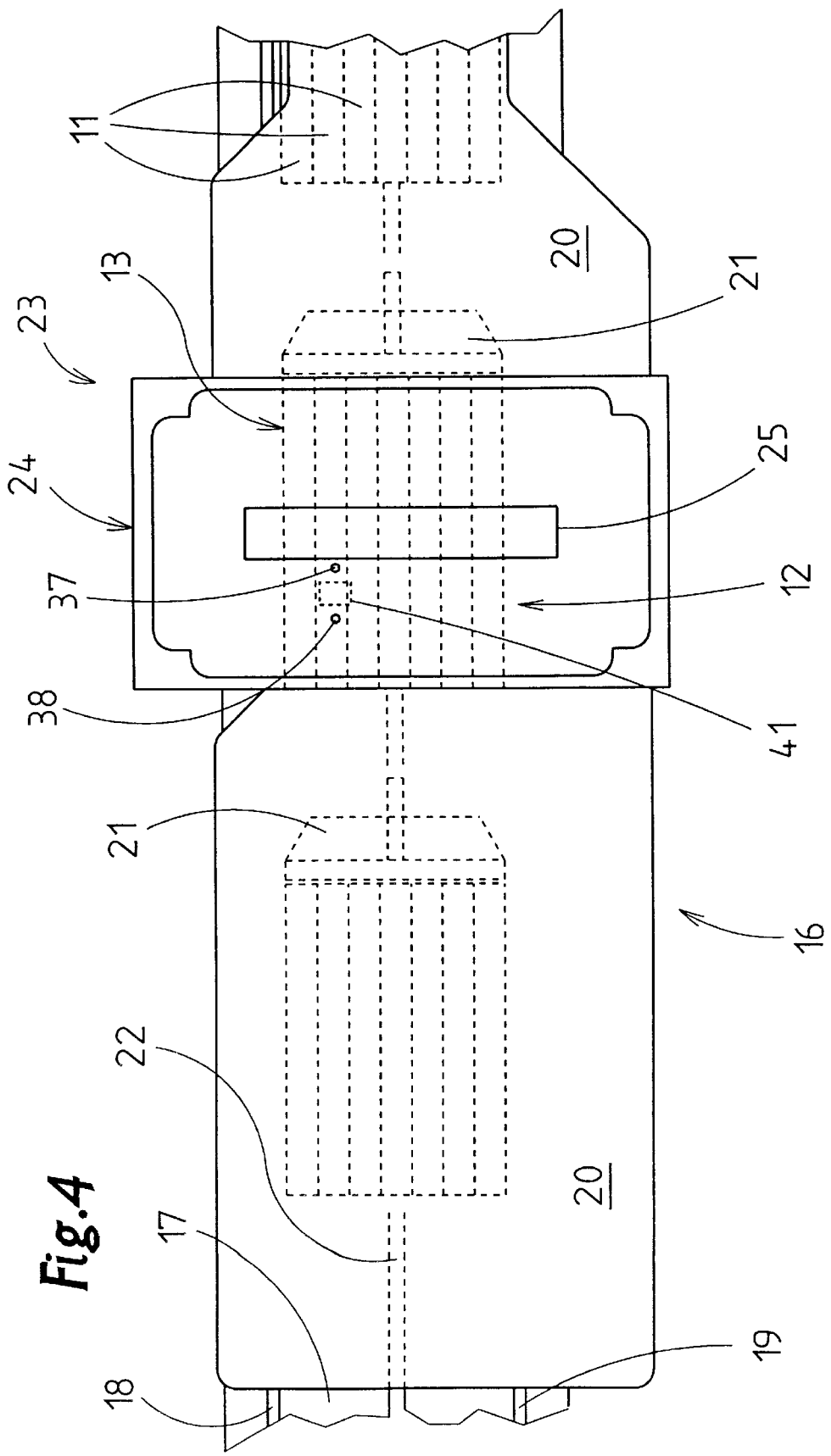
FIG. 4 shows the device in accordance with FIG. 1 in plan view.

The drawings show a plurality of exemplary embodiments or examples of use for monitoring or checking devices in which an elongated CCD linear array chip 10 is used as checking member to detect the surfaces or the contours of objects moving past the checking member, which are then processed by the evaluation unit (not shown). The objects are moved in this process transverse to the longitudinal extent of the CCD linear array chip 10. A profile, running transverse to the direction of movement, of the surface structure of the object is detected in this case on the basis of different brightness values. The objects can also be moved longitudinally in the longitudinal direction of the CCD linear array chip 10. Then a profile of the surface structure running along the direction of movement is recorded based on the different brightness values.

Alternatively, a varying structure of a fixed object can be detected on the basis of permanent or phased monitoring by means of a CCD linear array chip 10. All examples of use relate to the field of packaging technology, in particular cigarette packaging.

The exemplary embodiment represented in FIG. 1 to FIG. 5 relates to the monitoring of cigarettes 11, specifically of a cigarette group 12, which corresponds with respect to number and formation to the content of a cigarette pack. In the exemplary embodiment shown, the cigarette group 12 consequently comprises three layers 13, 14, 15. In accordance with the usual formation, the two outer layers 13 and 15 comprise seven, and the middle layer 14 six cigarettes 11. The latter are positioned in saddle position with reference to cigarettes 11 of the outer layers 13, 15.

The cigarette group 12 thus formed is transported along a cigarette track 16, the cigarettes being orientated in the direction of conveyance. In this case, the cigarette group 12 is situated on a lower track plate 17 between upright lateral guides 18, 19 and a top guide 20. The cigarette groups 12 are preferably conveyed continuously at a spacing from one another by drivers 21. The drivers 21 are mounted on endless conveyor members, for example on chains, and pass through a slot 22 in the track plate 17.

The cigarette groups 12 are moved past a checking set 23 arranged in the region of the cigarette track 16. Said set is positioned on the top side of the cigarette track 16, specifically in a cutout in the top guide 20. The checking set 23 comprises a housing 24, closed on all sides, with a checking opening 25 on the lower side facing the cigarette groups 12. The checking opening 25 extends in the shape of a slot over the full width of the cigarette group 12 or the cigarette track 16.

But the housing can also have a closing plate 25a arranged on the side of the checking opening 25. Said closing plate 25a is designed to be interchangeable and is removably connected to the housing 24 so that different closing plates 25 can be employed depending on the formed cigarette constellation or cigarette group 12.

A CCD linear array chip 10 is positioned as a checking member inside the checking set 23 or inside the housing 24, specifically with the longitudinal alignment transverse to the cigarette group 12 and therefore either perpendicular or parallel to the direction of movement. The CCD linear array chip 10 is configured such that the top side of the cigarette group 12 or the upper layer 13 is detected optically over the full width by the CCD linear array chip 10 as it passes by.

For this purpose, the CCD linear array chip 10 is arranged inside the housing 24 in a chamber or a holder 26 which has opposite the cigarettes 11 or the cigarette group 12 to be checked a through opening for light and/or optical signals. Arranged inside this through opening is an optical or lens-diaphragm system 27, that is to say in particular a lens, which focuses the image of the top side of the cigarette group 12 onto the CCD linear array chip 10, so that the latter can optically detect all the cigarettes 11 in the layer 13.

The checking set 23 comprises optical elements for optimum illumination of the object to be checked, that is to say of the upper region of the cigarette group 12. These are a plurality of, specifically four light sources 28, 29 which are arranged in pairs on mutually opposite sides inside the housing 24 and are connected here to the holder 26. Two light sources 28. 29 are positioned in each case on both sides of the track of movement of the cigarette group 12. Because of an inclined position of the light sources 28, 29, their light is directed in a specific way onto the cigarette group 12, to be precise in a fashion emphasizing bright and dark regions. The light sources 28, 29 are preferably LED elements with light in the infrared region.

The image, taken by the CCD linear array chip 10, of the top side of the cigarette group 12 is compared with a reference image in an evaluation unit. In the event of deviations owing to defective configuration of a cigarette group 12, an error signal is generated for segregating the relevant cigarette group from the production process. In the present case, the CCD linear, array chip 10 is connected to a mounting plate 30 which is arranged inside the checking set 23 or inside the housing 24 and which is a board. Processors, memories, etc. for evaluating the optoelectronic signal or the CCD linear array chip 10 can be arranged in the upper region of the housing 24.

Figure 5:
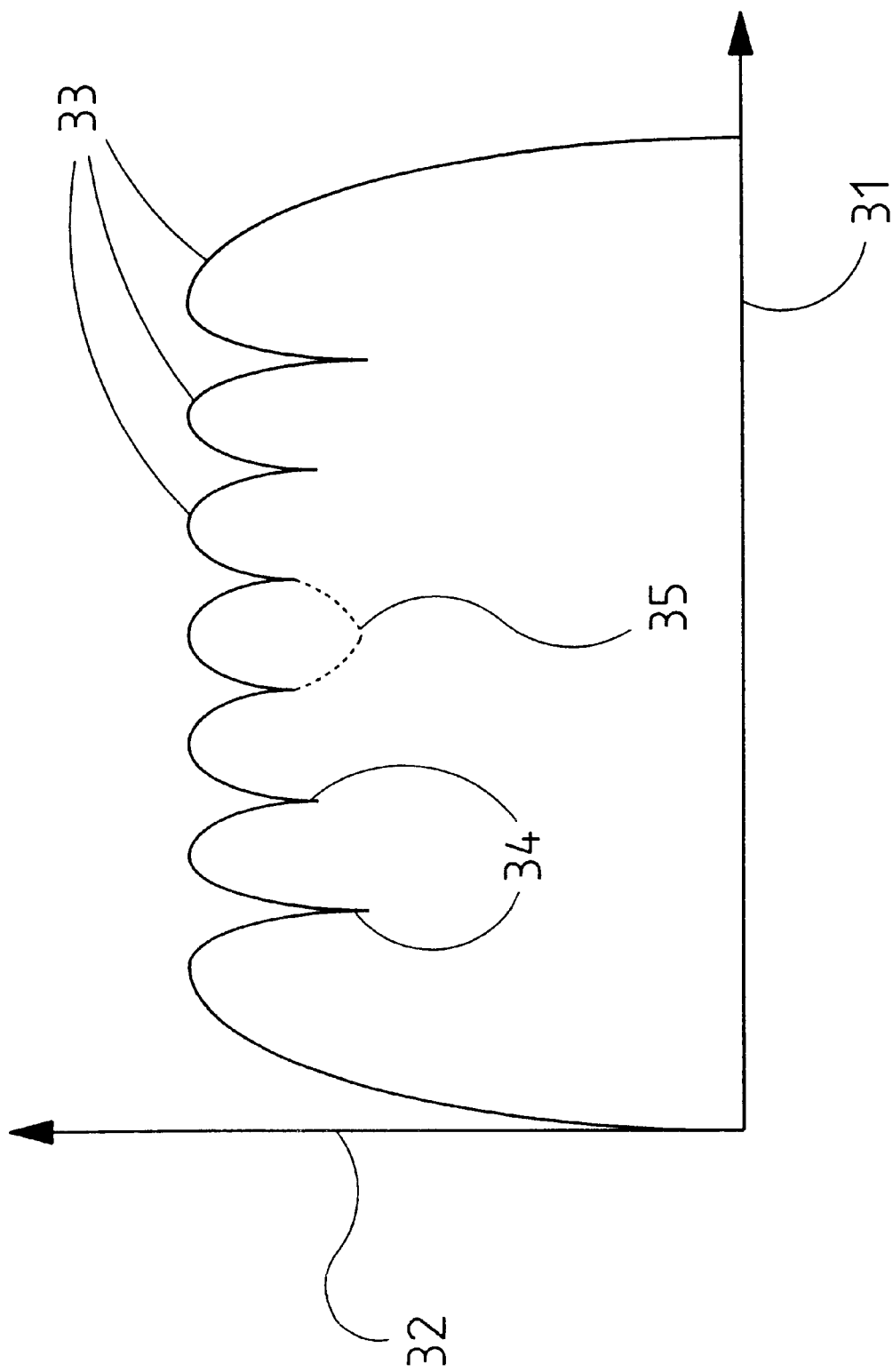
FIG. 5 shows a graph of a measured intensity signal of the device in accordance with FIGS. 1 to 4.

The image of the cigarette group 12 taken by the CCD linear array chip 10 is represented as a graph in FIG. 5 with respect to the variables which can be evaluated. Regions of different light intensity are produced on the basis of the illumination of the cigarette group 12. The cigarettes reflect light more strongly than do the gaps formed between the cigarettes. These differences in the light values are picked up and evaluated with the aid of the CCD linear array chip 10. The graph in accordance with FIG. 5 shows in the region of the abscissa 31 the juxtaposed light-sensitive elements of the CCD linear array chip 10, that is to say the CCD line. The measured light intensity is plotted on the ordinate 32. Crests 33 of the curve correspond in each case to a cigarette 11 which is present. Depressions 34 are the interspaces between the cigarettes 11. A dashed trough 35 is intended to indicate an image which is produced when a cigarette 11 is missing in the region of the upper layer 13. Moreover, it is assumed in the case of this checking method that a change in the upper, checked layer 13 always occurs when a cigarette 11 is missing at any point inside the formation of the cigarette group 12.

The checking set 23 or the CCD linear array chip 10 as checking member, and the light sources 28, 29 are not switched on continuously, but are activated cyclically in order to check one cigarette group 12 in each case. For this purpose, an optical tripping member 36 is arranged in the region of the checking set 23. Said member comprises an (optical) transmitter 37 and a receiver 38. The transmitter 37 generates a light barrier which is interrupted by the cigarette group 12 passing by, or—as in the present case—reflected and picked up by the receiver 38. The transmitter 37 and receiver 38 are connected via an optical fibre cable, specifically via a glass fibre bundle 39, to a light source, on the one hand, and the evaluation unit, on the other hand (for generating a switch-on signal). The transmitter 37, receiver 38 and the glass fibre bundle 39 are arranged in obliquely directed bores 40 of a lower wall of the housing 24.

However, the transmitter 37 and receiver 38 do not have to be connected by means of a glass fibre bundle 39 to a light source and the evaluation unit 38. Instead, the light source can represent the transmitter 38 and a photoelectric transformer can serve as the receiver 38. These electric components are protected by a glass pane positioned in front of them.

A depression 41 in the housing 24 permits the light barrier to pass through. The members, specifically the transmitter 37 and receiver 38, are therefore arranged set back with reference to the cigarette groups 12. The tripping member 36 is located downstream of the checking opening 25 in the direction of movement of the cigarette group 12. The tripping member 36 switches on the checking set 23 when the cigarette group 12 trips the light barrier with a region lying ahead in the direction of conveyance. As a result, checking of the cigarette group 12 is performed in a middle region—referred to the longitudinal extent of the cigarettes 11.

The tripping member 36 can be a reflection scanner, a one-way light barrier and/or a reflection light barrier if a transmitter and receiver, or a mirror, as the case may be, have been built into the track plate.

In an alternate embodiment, however, the tripping member 36 can also be omitted. In particular, this Is possible if an efficient evaluation unit, especially quick processors, are employed. The CCD linear array chip 10 then does not have to work in a clock-controlled mode. Instead it permanently records the image passing by. When the front area of the cigarette group is detected by the CCD line array chip 10, the corresponding (image) signal experiences a steep impulse edge, in particular a steep impulse slope. This impulse edge causes the evaluation unit to be turned on, or triggered, thus initiating the evaluation operation. Thus the tripping member 36 can be omitted, with the CCD linear array chip 10 working in a continuous move.

Figure 6:
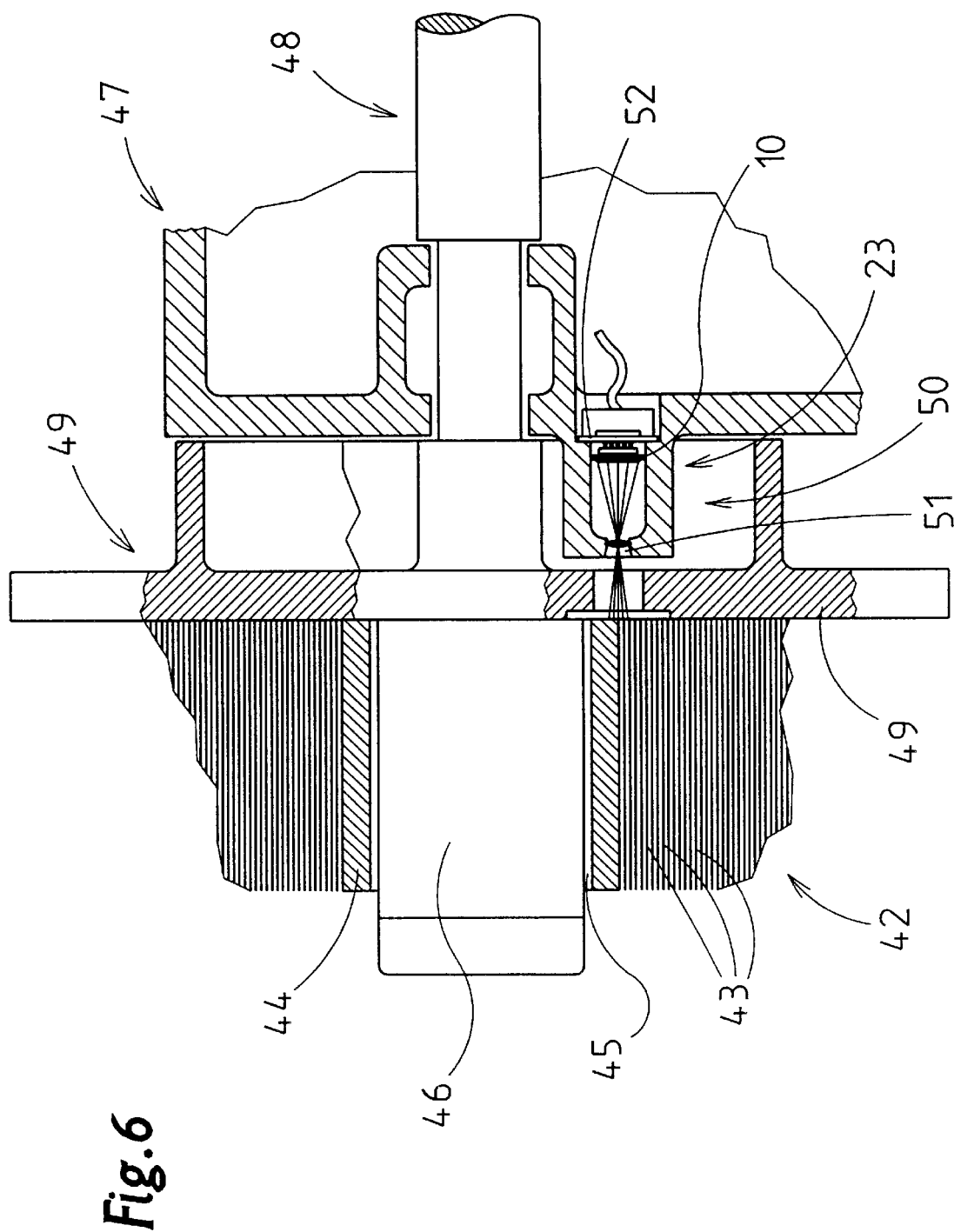
FIG. 6 shows a bobbin, wound material web—with checking device in radial section of the bobbin.
Figure 7:
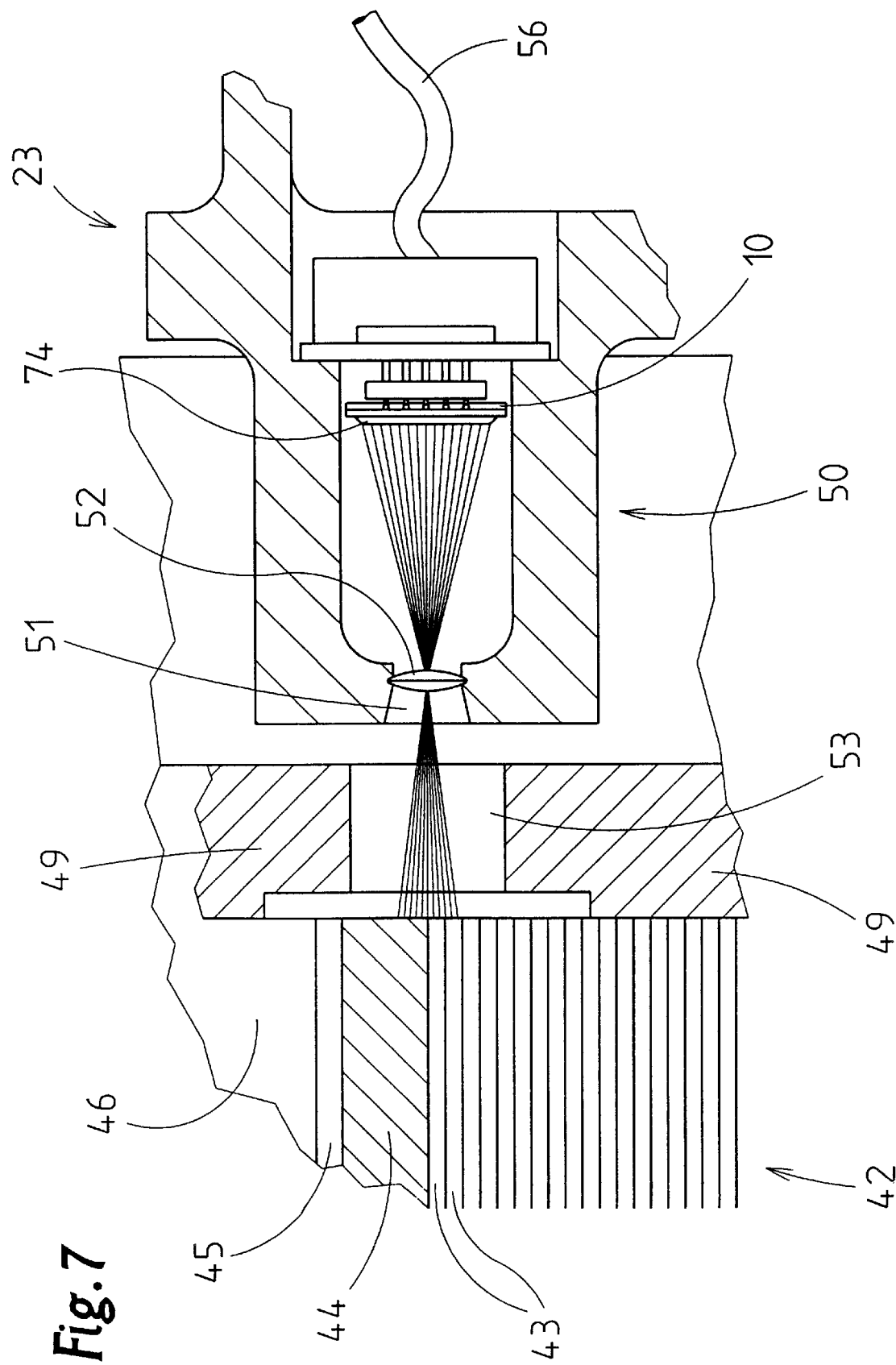
FIG. 7 shows the checking device of the exemplary embodiment in accordance with FIG. 6 on an enlarged scale.
Figure 8:
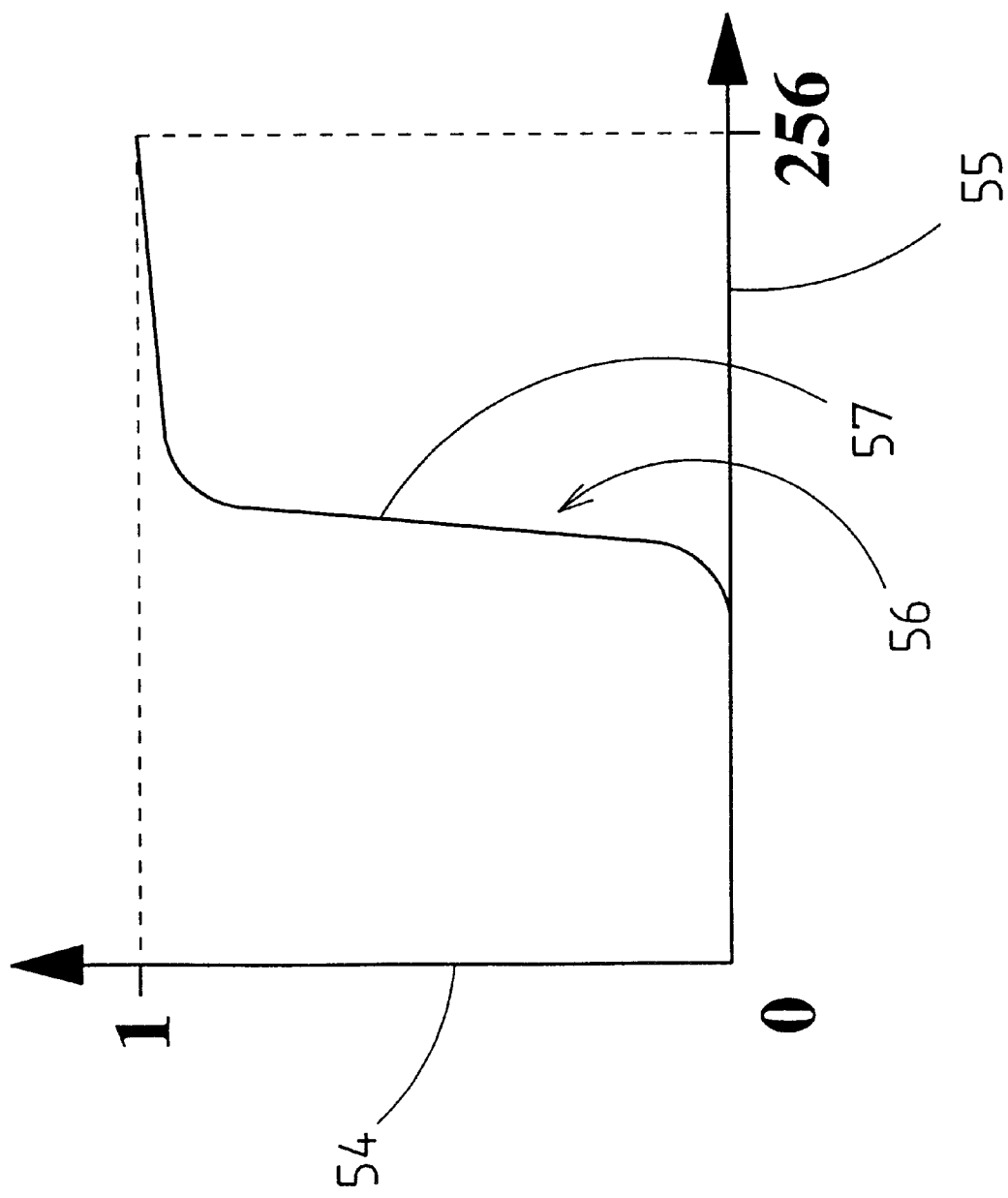
FIG. 8 shows the graph of a measured intensity signal of the device in accordance with FIGS. 6 and 7.

FIG. 6 to FIG. 8 provide a particular example of a checking device. This is the (continuous or cyclical) checking of a bobbin 42 composed of wound layers 43 of a material web. It concerns, chiefly packaging material, for example paper, film, tin foil or the like. The material web is wound onto a cylindrical bobbin core 44 for the purpose of forming the bobbin 42. Said core forms a central, circular middle opening 45.

For the purpose of processing the material web, the bobbin 42 is mounted on a holder, specifically on an, in particular, rotatable thrust journal 46 which enters the middle opening 45.

The checking set 23 monitors the consumption of the bobbin 42. In concrete terms, a residual section of the material web on the bobbin core 44 is determined when a new material web of a replacement bobbin is to be joined to the outgoing material web. It is to be taken into account when monitoring that the material web cannot or should not be allowed to be drawn off completely from the running bobbin 42. A residual section must be present for joining to a new material web upon inception of the connecting operation (splicing) on the bobbin 42 or the bobbin core 44 in such a way that the material web drawn off does not-lose tension and the remainder of the material web is possibly drawn off from the bobbin core 44.

The checking set 23 is positioned fixedly in the region of a bobbin holder. The latter comprises a support frame 47 which is supported non-rotatably on a shaft 48 connected to the thrust journal 46. The shaft 48 (driven rotatably) is connected to a supporting plate 49 against which the bobbin 42 bears with the bobbin core 44. The thrust journal 46 and the supporting plate 49 form a rotating unit.

The fixed support frame 47 forms a housing 50 for holding a checking member, specifically a CCD linear array chip 10. The housing 50 is arranged on the side, facing the bobbin 42, of the cup-shaped support frame 47. The housing 50 has a checking opening 51 on the side facing the bobbin 42. Provided inside the said checking opening is an optical system 52—lens—or a lens-diaphragm system for focusing light onto the CCD linear array chip 10.

The checking set 23 scans an end region of the material web, that is to say layers 43 facing the bobbin core 44. In concrete terms, a subregion of the winding or of the layers 43 and a subregion of the bobbin core 44 are optically detected. The supporting plate 49 is provided in this region with a through opening 53 aligned with the checking set 23. The optical checking consequently proceeds cyclically specifically at the instant when the through opening 53 rotating with the supporting plate 49 is situated opposite the checking set 23. A light source (not shown), in particular composed of LEDs, can be switched appropriately.

Because of the different brightness values of the light reflected by the layers 43 and the bobbin core 44, the CCD linear array chip 10 directed transverse to the layers 43 can determine the consumption of the material web and generate an appropriate signal for starting the splicing operation when a prescribed minimum number of layers 43 is reached. FIG. 8 shows a diagram in which the brightness values of the light acting on the individual sensors (pixels) of the CCD linear array chip 10 are plotted on the ordinate 54. The abscissa 55 shows the juxtaposed sensors or pixels of the CCD linear array chip 10 in a sequential enumeration. A plotted curve 56 is the light intensity assigned to the sensors/pixels of the CCD linear array chip 10. The left-hand region on the abscissa 55 shows that no light is picked up in the region of the bobbin core 44. An upper branch of the curve 56 exhibits increasing light intensity in the case of edge sensors/pixels, sensors arranged at the edge of the CCD linear array chip 10 already receiving the full light intensity. The monitoring member is set up such that the splicing operation is switched on in the case of a specific light intensity of a specific sensor 57, for example in the case of a sensor 57 of position 228 for a total of 256 sensors. The number of sensors or pixels, however, is essentially arbitrary. For a CCD chip it is preferably 256, but may also be 512, 1024, 2048, 4096 etc.

A further example relating to the theme of checking or monitoring follows from FIG. 9 to FIG. 12. This concerns the correct formation of a material web 58, for example composed of packaging material, such as film, paper or the like. The material web 58 is moved progressively, continuously past a checking set 23 of the type described, it being expedient to convey the material web 58 in the horizontal plane and to position the checking set 23 above the material web 58. The checking or monitoring extends in the present case to two features. On the one hand, there is correct guidance or positioning of the web edge 59. On the other hand, a marking or the like arranged on the top side of the material web 58 is to be checked, in the present case a material strip 60 running in the longitudinal direction of the material web 58 and connected to the material web 58. Said strip is, in particular, a tear-open strip for a wrapper composed of film material.

Figure 9:
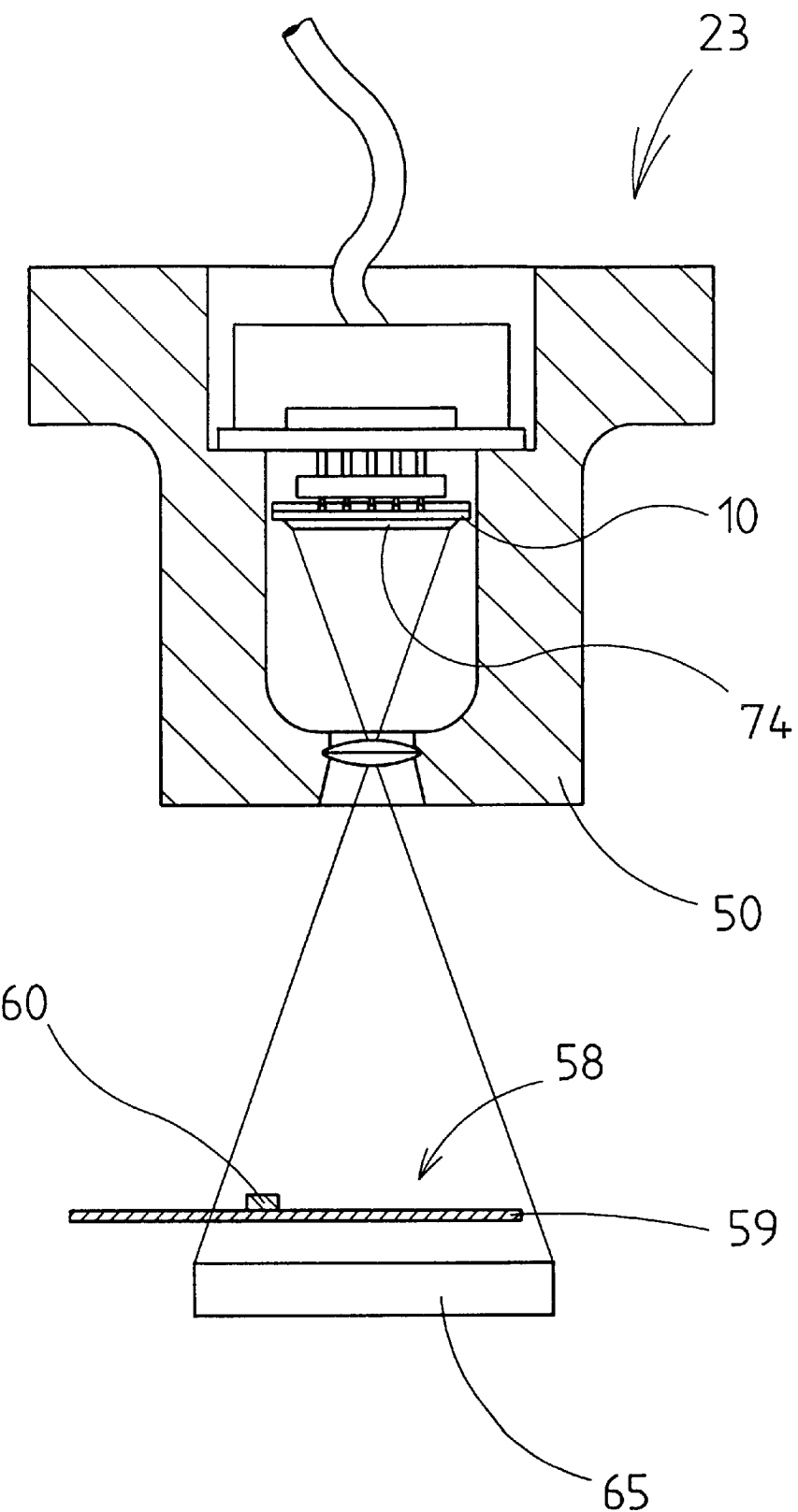
FIG. 9 shows a checking device for a material web in vertical section.
Figure 10:
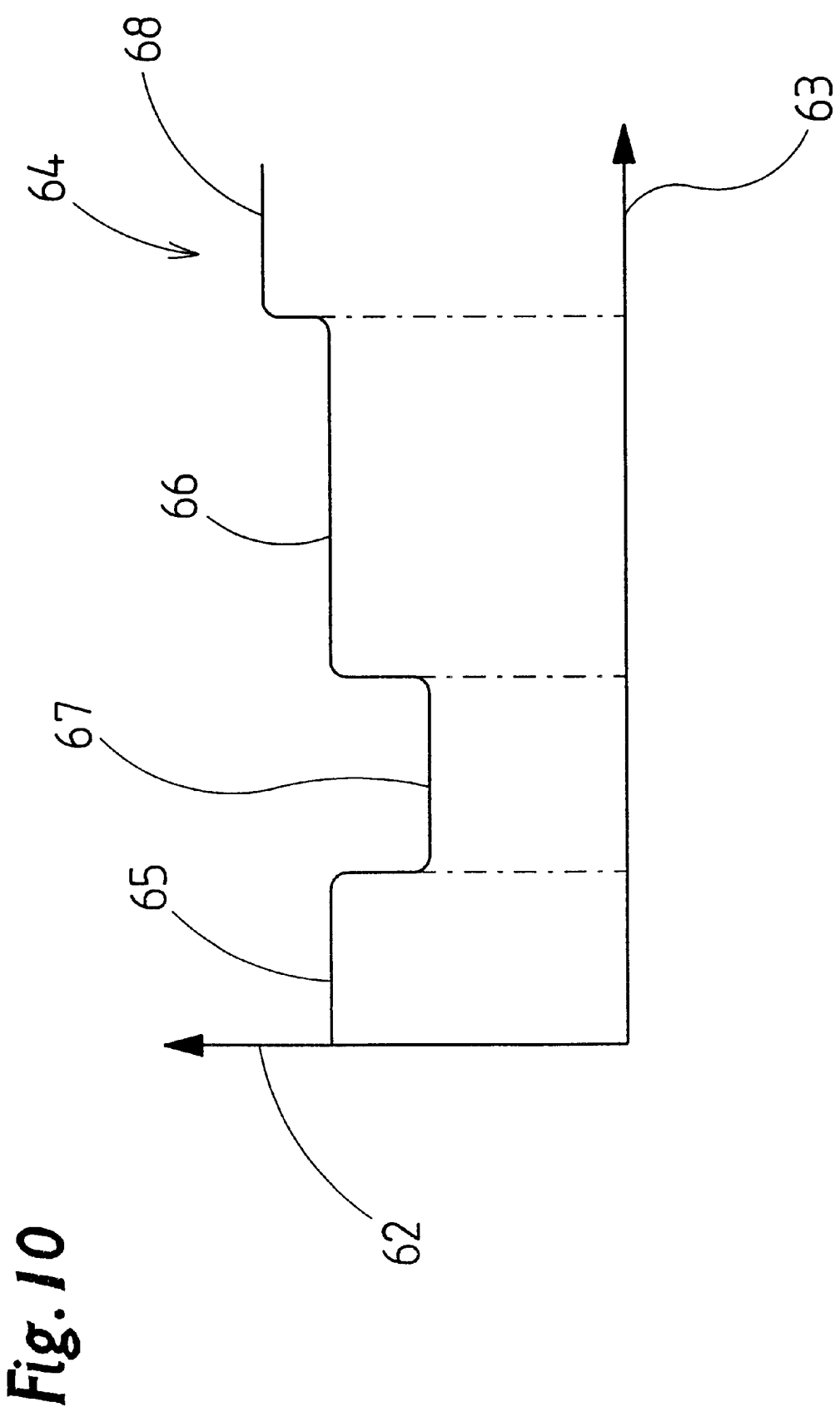
FIG. 10 shows the graph of a measured intensity signal of the device in accordance with FIG. 9.

The checking set 23 in accordance with FIG. 9 is constructed in the same or a similar way to the checking set 23 of FIG. 7. The CCD linear array chip 10 scans an edge region of the top side of the material web 58. A light source 61 is arranged in this example below the material web 58, with the result that the latter is illuminated on the side opposite the checking set 23. In the case of transparent material webs, the result is thus a curve in accordance with FIG. 10, in which, in turn, the light intensity is plotted on an ordinate 62, and the juxtaposed sensors or pixels of the CCD linear array chip 10 are plotted on an abscissa 63. A curve 64 corresponds to the brightness values picked up by the CCD linear array chip 10 in the case of correct formation of the material web. A first—seen from the left—curve segment 65 and a third curve segment 66 represent the light value in the region of the (uncoated) material web 58. Picked up in between is a curve segment 67 which exhibits a clearly lower light intensity and represents the position of the material strip 60. Finally, an edge curve segment 68 corresponds to the region outside the material web 58. Curved segments 65 . . . 68 must always exhibit the same prescribed width and position, given correct formation of the material web. Deviations of the light values picked up are produced from faulty positions of the material web 58 or the material strip 60.

It is also possible to use a transversely directed CCD linear array chip to check or monitor elongated objects at a plurality of regions by means of a single checking set 23. The exemplary embodiment in accordance with FIG. 11 and FIG. 12, concerns, in a fashion analogous to FIGS. 9 and 10, the checking of a material web 58 on a relatively long section, it being possible in accordance with FIG. 9 to check a plurality of external features, for example a material strip 60 and/or tear-open strip and/or a web edge 59.

In the embodiment in accordance with FIG. 9, the checking set 23 is positioned above the material web 58. A light source 61 is positioned offset relative to the checking set 23 below the material web 58. The region, situated between the checking set 23 and light source 61, of the material web 58 is detected by reflection of light, specifically by the arrangement of mirrors 69, 70, 71, 72 above and below the material web 58. The mirrors 69 . . . 72 are positioned such that the light beam 73 emanating from the light source 61 passes transversely through the material web 58 and is reflected on the opposite side of a first mirror 69, with the result that the light beam 73 passes through the material web 58 again in an inclined direction and onto the next mirror 70. The latter reflects the light beam 73 in the transverse direction onto a mirror 71, situated directly opposite, above the material web 58. A further mirror 72 below the checking set 23 transmits the light beam 73 onto the CCD linear array chip 10. The light is partially absorbed by the multiple passage through the web. The sensors of the CCD linear array chip 10 are set up for this purpose. Deviations on the basis of a faulty position of the material strip 60 lead to a change, which can correspondingly be recorded, in the light picked up in the region of the CCD linear array chip.

In the case of the checking sets 23 in accordance with FIGS. 6, 7 and in accordance with FIG. 9, a scattered light filter 74 is respectively arranged upstream of the CCD linear array chip 10 as a cover with an optical effect. This scattered light filter 74 is intended, in particular, to filter out short wave ambient light as a possible source of interference.

One particular advantage of the described system is that the evaluation of the image by the CCD chip can be adapted to any application by making changes to the software. Changes made to the software can be stored in the memory module of the evaluation unit.

LIST OF REFERENCE NUMERALS

| | |
|---|---|
| 10 | CCD linear array chip |
| 11 | Cigarette |
| 12 | Cigarette group |
| 13 | Layer |
| 14 | Layer |
| 15 | Layer |
| 16 | Cigarette track |
| 17 | Track plate |
| 18 | Lateral guide |
| 19 | Lateral guide |
| 20 | Top guide |
| 21 | Driver |
| 22 | Slot |
| 23 | Checking set |
| 24 | Housing |
| 25 | Checking opening |
| 25a | Closing plate |
| 26 | Holder |
| 27 | Optical system |
| 28 | Light source |
| 29 | Light source |
| 30 | Mounting plate |
| 31 | Abscissa |
| 32 | Ordinate |
| 33 | Crest |
| 34 | Depression |
| 35 | Trough |
| 36 | Tripping member |
| 37 | Transmitter |
| 38 | Receiver |
| 39 | Glass fibre bundle |
| 40 | Bore |
| 41 | Depression |
| 42 | Bobbin |
| 43 | Layer |
| 44 | Bobbin core |
| 45 | Middle opening |
| 46 | Thrust journal |
| 47 | Support frame |
| 48 | Shaft |
| 49 | Supporting plate |
| 50 | Housing |
| 51 | Checking opening |
| 52 | Optical system |
| 53 | Through opening |
| 54 | Ordinate |
| 55 | Abscissa |
| 56 | Curve |
| 57 | Sensor |
| 58 | Material web |
| 59 | Web edge |
| 60 | Material strip |
| 61 | Light source |
| 62 | Ordinate |
| 63 | Abscissa |
| 64 | Curve |
| 65 | Curve segment |
| 66 | Curve segment |
| 67 | Curve segment |
| 68 | Curve segment |
| 69 | Mirror |
| 70 | Mirror |
| 71 | Mirror |
| 72 | Mirror |
| 73 | Light beam |
| 74 | Scattered light filter |

What is claimed is:

1. A device for checking longitudinally extending cigarette groups (12), with respect to complete and correct formation thereof, in a checking set (23) that comprises a CCD chip, which has a number of light-sensitive checking elements, and an evaluation unit, characterized in that the CCD chip is a CCD linear array chip (10) that is directed in such a way, transverse to each cigarette group (12) to be checked, that a top side of the cigarette group (12) is detected over a full transverse width thereof, so that a transverse linear profile of the top side of the cigarette group (12) is detected by said CCD linear array chip (10) on the basis of light reflected from said top side.

2. The device according to claim 1, characterized in that the profile is detected by the CCD linear array chip (10) on the basis of different brightness values, and is compared in the evaluation unit with a standard reference representation.

3. The device according to claim 1, characterized in that each cigarette group to be checked or a region of the same which is to be checked is illuminated by light sources assigned to the checking set (23).

4. The device according to claim 1, characterized in that arranged upstream of the CCD linear array chip (10) is an optical system (27, 52) or lens-diaphragm system, by means of which an image taken of the cigarette group to be checked, or reflected light is focused onto the CCD linear array chip (10).

5. The device according to claim 1, characterized in that the CCD linear array chip (10) is directed with a longitudinal extent thereof transverse to a direction of movement of the group to be checked or transverse to a direction of a change to be monitored in the group.

6. The device according to claim 1, comprising means for conveying the cigarette groups in the longitudinal direction, and characterized in that said CCD linear array chip (10) is arranged above the cigarettes (11) which are being conveyed in their longitudinal direction.

7. The device according to claim 4, characterized in that the CCD linear array chip (10), together with the optical system (27, 52), is arranged in a housing (24, 50) which, on a side thereof facing the group to be checked, has an opening for detecting the groups to be checked.

8. The device according to claim 7, comprising means for cyclically actuating the checking set (23) in accordance with the the groups moving past the checking set (23) at intervals, there being assigned to the checking set (23) a tripping member (36) which is accommodated inside the housing (24) and detects a passing group in a non-contact fashion.

* * * * *